United States Patent
Samples, Jr.

(10) Patent No.: US 8,455,027 B2
(45) Date of Patent: Jun. 4, 2013

(54) METHOD AND SYSTEM FOR DETERMINING LEVEL OF DONENESS IN A COOKING PROCESS

(76) Inventor: Robert Hyram Samples, Jr., St. Augustine, FL (US)

(*) Notice: Subject to any disclaimer, the term of this patent is extended or adjusted under 35 U.S.C. 154(b) by 106 days.

(21) Appl. No.: 12/807,198

(22) Filed: Aug. 31, 2010

(65) Prior Publication Data
US 2011/0052767 A1   Mar. 3, 2011

Related U.S. Application Data (60) Provisional application No. 61/275,588, filed on Sep. 1, 2009.

(51) Int. Cl.
*A01K 43/00* (2006.01)

(52) U.S. Cl.
USPC ........... 426/231; 426/233; 426/520; 426/243; 426/523

(58) Field of Classification Search
USPC ............. 426/231, 520, 243, 233, 523; 99/325
See application file for complete search history.

(56) References Cited

U.S. PATENT DOCUMENTS

| | | | | |
|---|---|---|---|---|
| 4,171,382 | A * | 10/1979 | Buck | 426/243 |
| 6,299,921 | B1 * | 10/2001 | Loffler et al. | 426/233 |
| 6,439,768 | B1 * | 8/2002 | Wu et al. | 374/169 |
| 2007/0042091 | A1 | 2/2007 | Rund et al. | |
| 2007/0116084 | A1 | 5/2007 | Rund et al. | |
| 2008/0031302 | A1 | 2/2008 | Rund et al. | |
| 2008/0056328 | A1 | 3/2008 | Rund et al. | |

FOREIGN PATENT DOCUMENTS
GB    2203320    * 12/1988

* cited by examiner

*Primary Examiner* — Drew Becker
*Assistant Examiner* — Preston Smith
(74) *Attorney, Agent, or Firm* — Thomas C. Saitta (57) ABSTRACT

A method and apparatus for determining when meat is cooked to a desired degree of doneness, the method continuously calculating the arithmetic integral of the meat's temperature (T) minus some threshold temperature ($T_t$) to determine an Energy Impulse (EI) value. Each level of doneness for a particular type of meat is represented by a range of EI values resulting from the integration of a time-based function of the meat's temperature. When the desired EI value is reached, the meat has been cooked to the desired doneness level, a signal is generated that indicates the meat is cooked to the desired doneness level and the cooking process is terminated.

12 Claims, 6 Drawing Sheets

METHOD AND SYSTEM FOR DETERMINING LEVEL OF DONENESS IN A COOKING PROCESS

This invention claims the benefit of U.S. Provisional Patent Application Ser. No. 61/275,588, filed Sep. 1, 2009.

BACKGROUND OF THE INVENTION

This invention relates generally to the field of cooking systems and processes, and more particularly relates to the field of such systems and processes for cooking meat, and even more particularly relates to such systems and processes for accurately cooking the meat to a desired level or degree of doneness and/or accurately determining the level or degree of doneness.

The common method for determining the level of doneness of meat is to measure the internal temperature of the meat using a thermo-probe that is inserted into the meat during the cooking process. When the internal temperature reaches a pre-determined value (e.g., for beef, well done=170 degrees, medium well=165 degrees, medium=160 degrees, medium rare=145 degrees and rare=135 degrees), the meat is considered properly cooked. This approach to determining the doneness of meat, however, generally results in over-cooked meat. Experiments suggest this approach is wrong as much as 75% of the time.

This invention contends the doneness of meat can be better determined by applying a function of time and temperature to the doneness determination. The transition from raw meat to meat cooked to various levels of doneness is actually a chemical reaction initiated by adding heat to the meat. As with most chemical reactions, the reaction rate is a function of temperature and the degree of completeness of the reaction is a function of time and temperature. This approach has been shown to be accurate more than 90% of the time. Of importance is the fact that this methodology accounts for variations and fluctuations of external temperature during the cooking process, which may result from movement of the meat to different locations on the cooking equipment, opening and closing the cover of a bar-b-que grill, etc.

BRIEF SUMMARY

The invention is a methodology and associated apparatuses for performing the method of accurately determining the doneness level of meat during the cooking process, the method comprising the steps of inserting a temperature probe or thermo-probe into the meat, measuring the temperature of the meat continuously or intermittently at relatively tiny time intervals, transmitting the temperature data to a computing device, calculating the arithmetic integral of the temperature-time function to determine a real-time Energy Impulse (EI) value, comparing the calculated EI value to a range of pre-determined EI values to determine the degree of doneness of the meat, and generating a signal to indicate that the cooking process should be terminated.

DETAILED DESCRIPTION OF THE INVENTION

With reference to the drawings, the best mode and the preferred embodiment or embodiments of the invention will now be described in detail. In a most general sense, the invention is a method of accurately determining the degree or level of doneness of meat during a cooking process, the methodology requiring a system comprising a thermo-probe adapted for insertion into the meat during the cooking process, the thermo-probe constructed such that it may remain continuously inserted in the meat. The system further comprises means to transmit the internal temperature of the cooking meat to a calculating/computing device, such as a custom integrated circuit chip, microprocessor, computer or the like possessing software to calculate the arithmetic integral of an arithmetic function based on the temperature vs. time data transmitted from the meat, means to compare the calculated integral value to pre-determined values for varying ranges of doneness in the meat being cooked, and means to generate a signal when the calculated EI value approximates the pre-determined EI value for a desired degree of doneness such that the cooking process should be stopped The methodology comprises the steps of inserting the thermo-probe into the meat to be cooked, placing the meat into a cooking environment, such as in an oven, or a grill, on a griddle, etc., and delivering heat to the meat to initiate and sustain the cooking process. The internal temperature of the meat is monitored continuously or intermittently in relatively tiny time intervals to produce temperature data, which is transmitted to a computing device capable of computing the arithmetic integral of the temperature vs. time function during the cooking process. The value of the integral, referred to herein as the Energy Impulse (EI) value, is compared to a pre-determined range of EI values for a given type of meat. When the calculated EI value is substantially equal to the pre-determined EI value or range of values for a chosen degree of doneness, a signal is generated indicating the process should be halted as the meat is now cooked to the desired degree.

The basic form of the equation used to determine the Energy Impulse value is:

$$EI = \int (T_d(t)^2 + T_d(t)) \cdot dt \text{ when } T(t) >= T_t(t)$$

where $T_d(t) = T(t) - T_x(t)$.

In this equation, T(t) represents the temperature measured within the meat as it is being cooked, and $T_x(t)$ represents a threshold temperature, which may be zero, but preferably is taken to be the minimum temperature at which the cooking chemical reaction is initatied, such as for example 100 degrees for beef.

A more precise form of the equation for determining the Energy Impulse value is:

$$EI = a \cdot \int (b \cdot T_d(t)^2 + c \cdot T_d(t) + f) \cdot dt \text{ when } T(t) >= T_t(t)$$

where a, b, c, and f are constants.

Constants a, b, c and f are chosen to manipulate the resulting value to standardize the resulting EI value.

The formulas above calculate the area under the curve created by subtracting the threshold temperature ($T_t$) from the continuously measured meat temperature (T), once the temperature has exceeded the threshold temperature. The area under the curve is mathematically equivalent to the integral of the curve. Therefore the area under the curve is equivalent to EI.

Experiments have shown that when the integral of the meat's temperature (T) minus some threshold temperature ($T_t$) is greater than a given value X but less than a given value Y, then the meat is cooked to a particular doneness level. As an example, when cooking beef using a time-temperature EI formula with a=1, b=0, c=0.001 and f=0, the following EI units, within a range of plus or minus 3 are typical: rare=3, medium rare=7, medium=16, medium well=28 and well done=35. These EI values are typically attained well before the traditional internal temperature minimum for each doneness level is reached.

Figure 1:
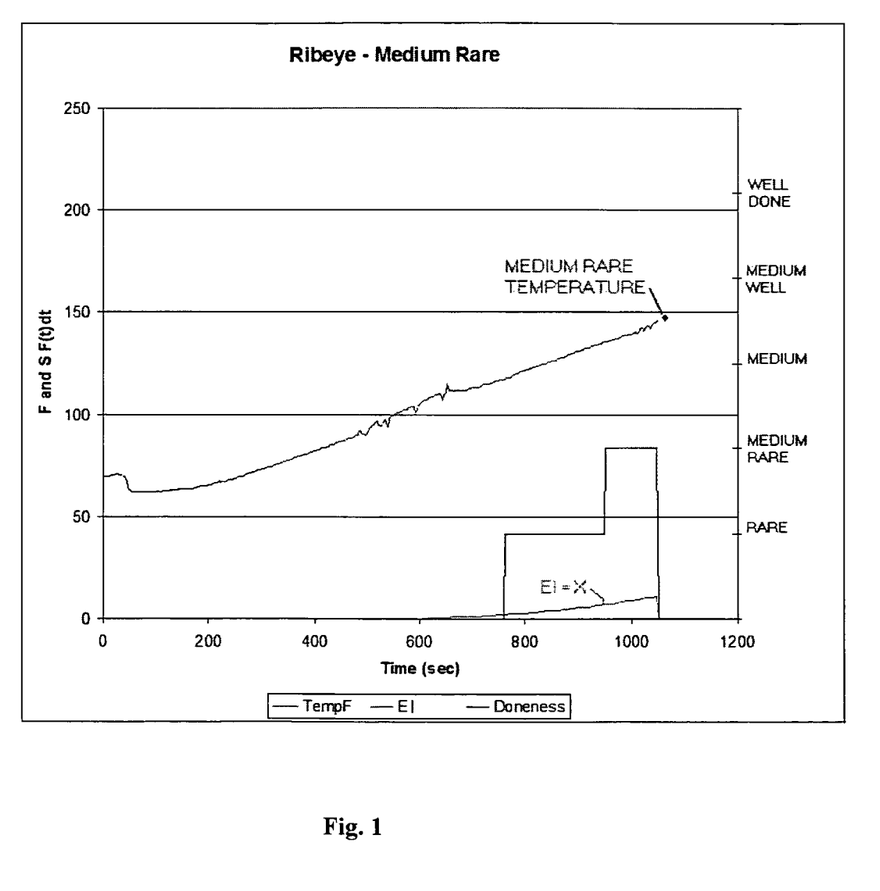
FIG. 1 is a graphical illustration showing temperature vs. time data for beef during a cooking process and Energy Impulse (EI) values as calculated during the cooking process.
Figure 2:
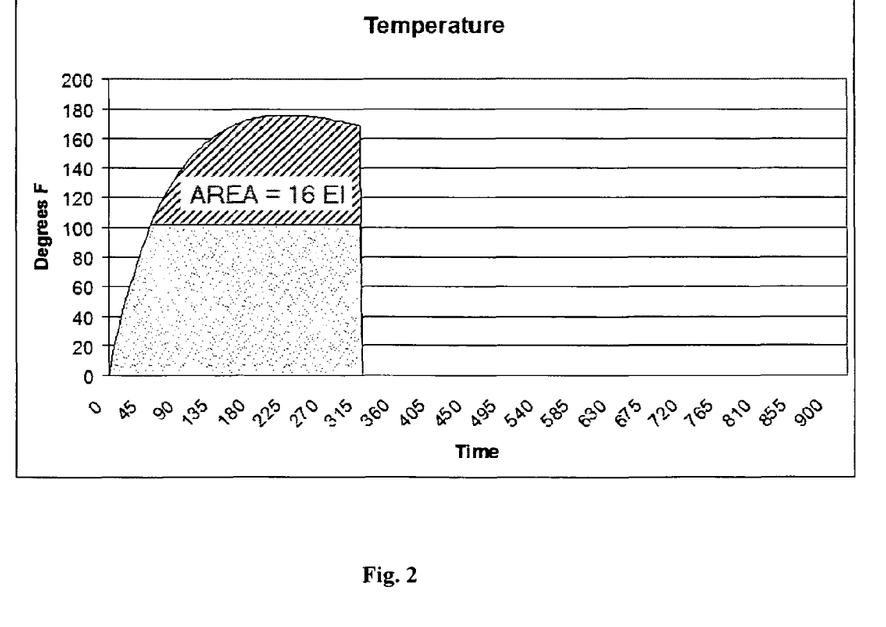
FIGS. 2 through 5 are graphical illustrations showing the variation in time required to reach identical EI values under different cooking scenarios.
Figure 3:
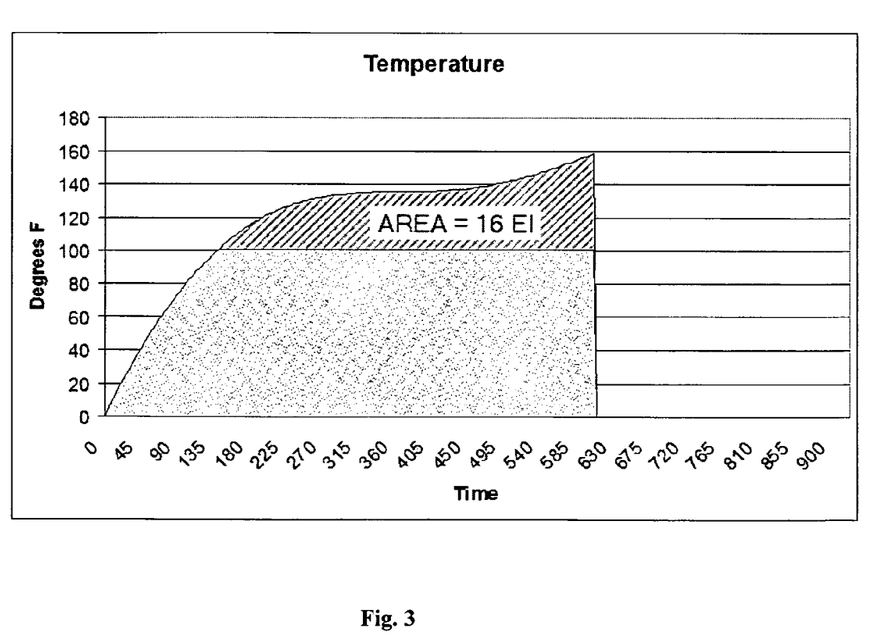
Figure 4:
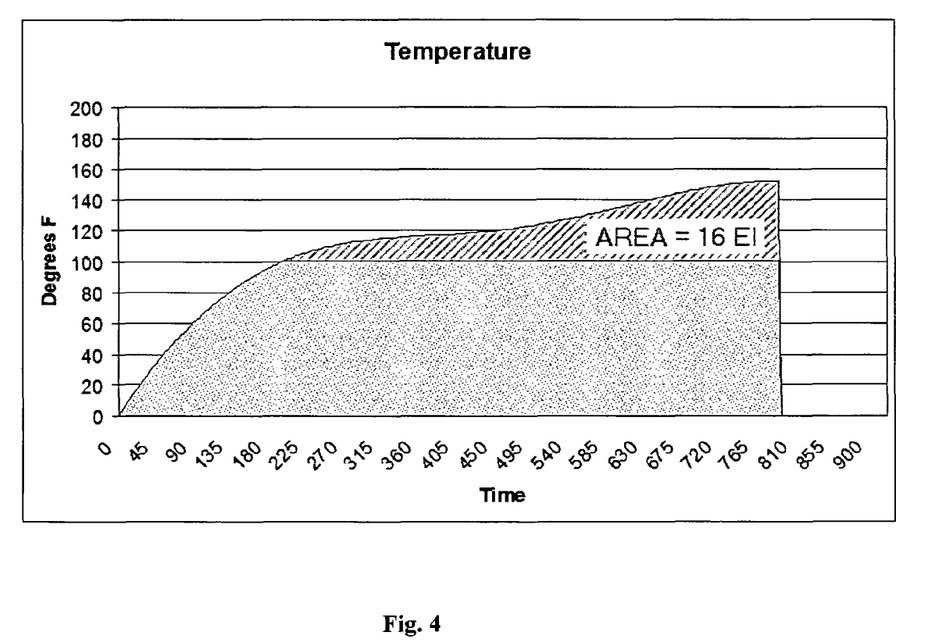
Figure 5:
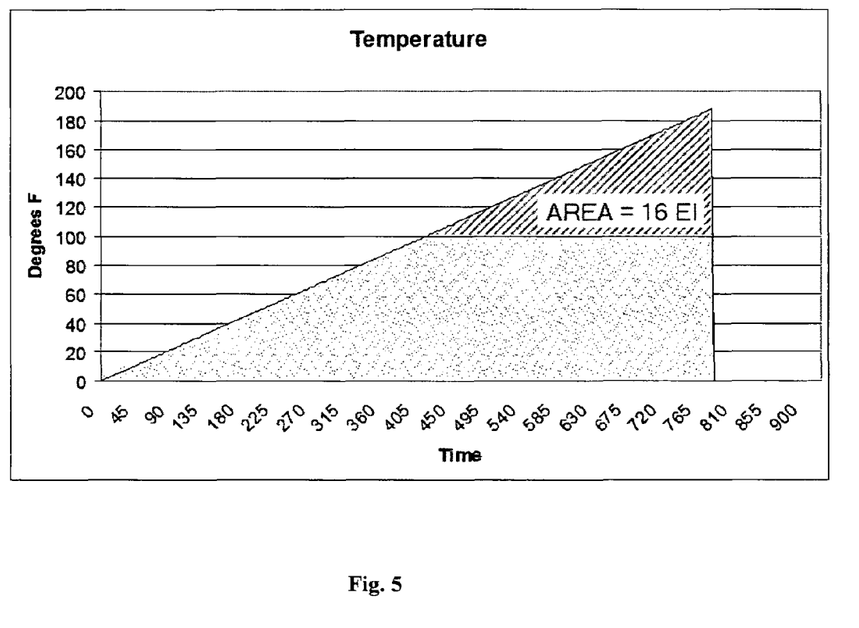

This is illustrated in FIG. 1, which shows a cooking scenario for producing a medium rare piece of beef. As time proceeds, the internal temperature T rises in a relatively steady manner, as shown by the rising line on the temperature vs. time scale. Under the typical protocol for determining doneness, the meat is considered to be medium rare when the internal temperature reaches approximately 145 degrees, which in this instance occurs at approximately 1060 seconds of cooking time The right side scale shows the doneness of the meat as determined using the EI for this meat. As shown in the lower right quadrant of the graph, the EI value of the cooking meat attains the EI value for medium rare at approximately 950 seconds of cooking time, over 100 seconds prior to the internal temperature reaching 145 degrees—meaning that in this instance the beef would likely have been overcooked. Had the meat been removed from the heat source when the proper EI value was reached, the meat would have been properly cooked.

Regardless of how the meat is cooked or the temperature profile created by the cooking process, the use of EI to determine the doneness level is superior to using only the meat temperature. As an example, the FIGS. 2 through 5 illustrate various time-temperature cooking profiles for cooking beef to a medium level of doneness. In each case the meat is cooked until the EI reaches the same value (in these examples EI=16). In each case the meat was cooked to the same doneness level, regardless of the temperature profile, i.e., regardless of variations in external heating temperature such as would result from variations in heat supply, movement of the meat to different locations on the cooking apparatus, temperature fluctuations resulting from opening and closing a bar-b-que grill cover, etc.

Figure 6:
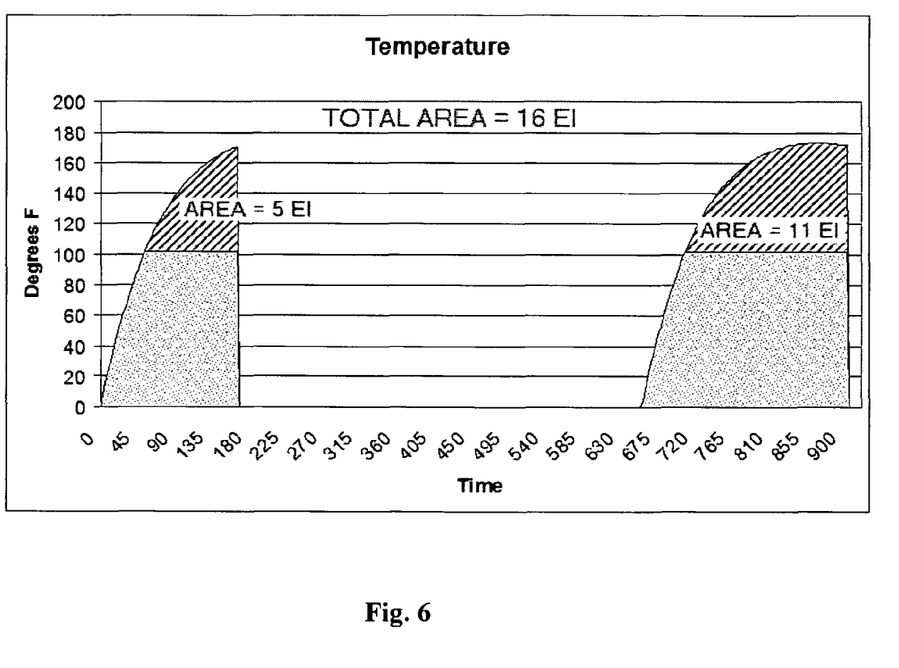
FIG. 6 is a graphical illustration of a showing an interrupted cooking process with the two EI values added to produce a desired EI value.

Another benefit of using Energy Impulse to determine meat doneness is that the meat can be cooked in multiple sessions. As an example, the meat can be cooked to a low, non-zero, EI level and then quickly cooled or frozen. The final EI level can be recorded and printed on the meat's packaging. At a later time the meat can be reheated by reinserting the device's temperature probe into the meat, informing the controller of the meat's original EI level and then applying heat to the meat. The device will begin calculating the total EI that has been applied to the meat using the original EI as a starting point instead of zero. This is illustrated in FIG. 6. When the total calculated EI matches the EI required for a desired doneness, then the meat can be served with the confidence that it is cooked to the desired level. Had temperature been used as the doneness criteria the meat would have been overcooked.

Pork and poultry must be adequately cooked to ensure the meat is not contaminated with bacteria or other illness causing organisms. Typically the USDA recommends cooking these meets to certain internal temperatures to be considered safe to consume. As an example, the USDA recommends cooking chicken to 165° F. to be considered safe to eat. The USDA also recognizes that meat can be considered safe to consume if held at lower temperatures for some period of time. As an example, based on data presently provided by the USDA, chicken with 12% fat can be considered safe to consume if the internal temperature has been at 145° F. for 13 minutes. Simply using a single temperature to determine if the meat is safe to consume, such as the USDA's 165° F. for chicken, generally results in dry, over-cooked meat. It is also difficult and often impractical to hold the meat's internal temperature at a constant level for a period of time.

When cooking meat, the internal temperature gradually increases. Once the meat reaches a minimum temperature, harmful microorganisms (such as salmonella) within the meat start to die. As the temperature increases, the death rate of the harmful microorganisms increases. The USDA has established a time, for each temperature above the minimum temperature, at which a certain quantity of harmful bacteria has been killed. The meat can generally be considered safe if held at the given temperature for at least the specified amount of time for a given degree of contamination.

Since the temperature within the meat does not instantly reach the desired temperature but rather gradually increases, the meat begins to cook before the meat's internal temperature reaches the desired sterilization temperature. This can cause the meat to be overcooked before the required sterilization time has been reached for the desired sterilization temperature. A percentage of any bacteria that may be in the meat dies even at lower cooking temperatures, if the temperature is above the USDA specified minimum temperature. This means some of the bacteria die while the meat's internal temperature is increasing to the desired sterilization temperature. Since some of the bacteria have died before the desired sterilization temperature has been reached, the meat can be considered safe to consume, even before the USDA specified time for the given temperature has elapsed.

Furthermore, it is possible for the meat to be considered safe to eat before the meat has reached a desired cooking doneness level, as determined in invention #1 or the USDA recommended cooking temperature (e.g. 165° F. for chicken). As an example, if the USDA recommends chicken cook at 136° F. for 81.4 minutes to be considered safe and if it takes 10 minutes for the chicken's temperature to rise from 136° F. to 137° F., then 12.3% of the bacteria have been killed during this time. Now there is only 87.7% of the original bacteria remaining alive. If the USDA recommends the chicken cook for 65.5 minutes at 137° F. to be considered safe and if it takes 10 minutes for the chicken's temperature to increase from 137° F. to 138 F, then 15.3% more of the bacteria has died. Now there is only 62.3% of the bacteria left. These calculations repeat until the results indicate enough of the bacteria have been killed to be considered safe to consume. This results in having meat that is safe to eat but that has been cooked to a lower temperature and has not been overcooked. After the meat is considered safe to consume, cooking can continue until the meat is cooked to the desired doneness level as determined by the EI method discussed above.

An apparatus can combine both determination processes discussed above to determine when meat is correctly cooked to a desired level and safe to consume. The device can be a single device equipped with a sensor to measure the internal temperature of the meat, a display to indicate the cooking parameters and level of doneness as well as a means to select the desired doneness level. The device will also incorporate a means, such as a digital microprocessor or an analog circuit, to perform the necessary calculations and send the results of the calculation to the display on the device. Since different types of meat (such as pork and poultry) are likely to have different Energy Impulses for a desired doneness than beef, as well as different kill rates for any contaminating organisms, there should also be a means of telling the device which type of meat is being cooked. The temperature measuring sensor may also be separate from the main device, connected to it via a wire or radio transmitter. Additional temperature sensors can be connected to the device, allowing it to monitor the temperature and calculate the doneness level and degree of decontamination of several food items at the same time.

These devices can be used with any form of cooking or cooking device. It has been shown to work well when baking meat in an oven, broiling in an oven or a barbecue grill, boiling or cooking on a stovetop or griddle. It also works well in slow cooking environments such as crockpots and meat smokers.

An exemplary embodiment of a device used to implement these methodologies may comprise one or more temperature measuring probe(s) (such as but not limited to thermocouples, thermistors or RTDs), a computational device(s) (such as but not limited to a computer or analog circuit designed to execute the necessary calculations or operations) and at least one interface device.

The interface device allows a person to select the type of meat being processed and the desired doneness level. The interface device will also be used to inform the person operating it of the present doneness level of the meat as well as an estimate of when the meat will reach a given level of doneness. The interface device(s) may be separate from or integrated into the computational device(s).

The temperature measuring probe(s) are used to measure the internal temperature of the meat being processed and transmit that temperature value to the computational device(s) for processing.

The computational device(s) will process the measured temperature(s) and the data input via the interface device(s) to calculate the EI of the meat and determine the doneness level of the meat. The computational device(s) may also use these same parameters to determine when the meat has reached USDA recommended levels of sanitation.

It is understood that equivalents and substitutions for certain elements set forth above may be obvious to those of ordinary skill in the art, and therefore the true scope and definition of the invention is to be as set forth in the following claims.

I claim:

1. A method of accurately determining the degree of doneness of meat during a cooking process comprising the steps of:
    inserting a thermo-probe into meat to be cooked,
    placing the meat into a cooking environment,
    delivering heat to the meat to initiate and sustain the cooking process,
    monitoring the internal temperature of the meat during the cooking process to produce temperature data,
    transmitting the temperature data to a computing device capable of computing the arithmetic integral of an arithmetic function based on the temperature vs. time data during the cooking process,
    calculating the arithmetic integral of an arithmetic function based on the temperature vs. time data on a continuous basis to produce an energy impulse value (EI),
    comparing the calculated EI value to a pre-determined scale of EI values representing EI values for differing degrees of doneness, and
    generating a signal when the calculated EI value approximates the pre-determined EI value for a desired degree of doneness such that the cooking process should be stopped,
    wherein said step of calculating the arithmetic integral of the temperature vs. time data is performed using the equation $EI=\int(T_d(t)^2+T_d(t))\cdot dt$ when $T(t)>=T_t(t)$, where $T_d(t)=T(t)-T_t(t)$, and $T(t)$ represents the temperature measured within the meat as it is being cooked, and $T_t(t)$ represents a threshold temperature.

2. The method of claim 1, wherein said steps of monitoring and transmitting the internal temperature of the meat is performed continuously.

3. The method of claim 1, wherein said threshold temperature is the temperature at which the meat begins to cook.

4. A method of accurately determining the degree of doneness of meat during a cooking process comprising the steps of:
    inserting a thermo-probe into meat to be cooked,
    placing the meat into a cooking environment,
    delivering heat to the meat to initiate and sustain the cooking process,
    monitoring the internal temperature of the meat during the cooking process to produce temperature data,
    transmitting the temperature data to a computing device capable of computing the arithmetic integral of an arithmetic function based on the temperature vs. time data during the cooking process,
    calculating the arithmetic integral of an arithmetic function based on the temperature vs. time data on a continuous basis to produce an energy impulse value (EI),
    comparing the calculated EI value to a pre-determined scale of EI values representing EI values for differing degrees of doneness, and
    generating a signal when the calculated EI value approximates the pre-determined EI value for a desired degree of doneness such that the cooking process should be stopped,
    wherein said step of calculating the arithmetic integral of the temperature vs. time data is performed using the equation $EI=a\cdot\int(b\cdot T_d(t)^2+c\cdot T_d(t)+f)\cdot dt$ when $T(t)>=T_t(t)$, where a, b, c, and f are constants chosen to manipulate the resulting value to standardize the resulting EI value.

5. The method of claim 4, wherein said threshold temperature is the temperature at which the meat begins to cook.

6. The method of claim 4, wherein said steps of monitoring and transmitting the internal temperature of the meat is performed continuously.

7. A method of accurately determining the degree of doneness of meat during a cooking process comprising the steps of:
    inserting a thermo-probe into meat to be cooked,
    placing the meat into a cooking environment,
    delivering heat to the meat to initiate and sustain the cooking process,
    monitoring the internal temperature of the meat during the cooking process to produce temperature data,
    transmitting the temperature data to a computing device capable of computing the arithmetic integral of the meat's internal temperature vs. time data during the cooking process,
    calculating the arithmetic integral of the meat's internal temperature vs. time data on a continuous basis to produce an energy impulse value (EI), comparing the calculated EI value to a pre-determined scale of EI values representing EI values for differing degrees of doneness, and stopping the cooking process when the calculated EI value approximates the pre-determined EI value for a desired degree of doneness, wherein said step of calculating the arithmetic integral of the temperature vs. time data is performed using the equation $EI=\int (T_d(t)^2 + T_d(t)) \cdot dt$ when $T(t)>=T_t(t)$, where $T_d(t)=T(t)-T_t(t)$, and $T(t)$ represents the temperature measured within the meat as it is being cooked, and $T_t(t)$ represents a threshold temperature.

8. The method of claim 7, wherein said threshold temperature is the temperature at which the meat begins to cook.

9. The method of claim 7, wherein said steps of monitoring and transmitting the internal temperature of the meat is performed continuously.

10. A method of accurately determining the degree of doneness of meat during a cooking process comprising the steps of:

inserting a thermo-probe into meat to be cooked, placing the meat into a cooking environment, delivering heat to the meat to initiate and sustain the cooking process, monitoring the internal temperature of the meat during the cooking process to produce temperature data, transmitting the temperature data to a computing device capable of computing the arithmetic integral of the meat's internal temperature vs. time data during the cooking process, calculating the arithmetic integral of the meat's internal temperature vs. time data on a continuous basis to produce an energy impulse value (EI), comparing the calculated EI value to a pre-determined scale of EI values representing EI values for differing degrees of doneness, and stopping the cooking process when the calculated EI value approximates the pre-determined EI value for a desired degree of doneness, wherein said step of calculating the arithmetic integral of the temperature vs. time data is performed using the equation $EI = a \cdot \int (b \cdot T_d(t)^2 + c \cdot T_d(t) + f) \cdot dt$ when $T(t)>=T_t(t)$, where a, b, c, and f are constants chosen to manipulate the resulting value to standardize the resulting EI value.

11. The method of claim 10, wherein said threshold temperature is the temperature at which the meat begins to cook.

12. The method of claim 10, wherein said steps of monitoring and transmitting the internal temperature of the meat is performed continuously.

* * * * *